(12) United States Patent
Roche

(10) Patent No.: US 8,372,147 B2
(45) Date of Patent: Feb. 12, 2013

(54) METHOD FOR DETECTING BODY PARAMETERS

(76) Inventor: Martin W. Roche, Fort Lauderdale, FL (US)

( * ) Notice: Subject to any disclaimer, the term of this patent is extended or adjusted under 35 U.S.C. 154(b) by 197 days.

(21) Appl. No.: 13/014,767

(22) Filed: Jan. 27, 2011

(65) Prior Publication Data

US 2011/0118565 A1    May 19, 2011

Related U.S. Application Data

(62) Division of application No. 11/391,988, filed on Mar. 29, 2006, now Pat. No. 7,918,887.

(60) Provisional application No. 60/665,797, filed on Mar. 29, 2005, provisional application No. 60/763,869, filed on Feb. 1, 2006, provisional application No. 60/763,761, filed on Feb. 1, 2006.

(51) Int. Cl.
*A61F 2/44* (2006.01)
(52) U.S. Cl. .................................. 623/17.11
(58) Field of Classification Search ............... 623/22.11; 606/86, 96, 93, 94, 102
See application file for complete search history.

(56) References Cited

U.S. PATENT DOCUMENTS

| | | | |
|---|---|---|---|
| 4,936,308 A * | 6/1990 | Fukukita et al. ............... 600/438 |
| 5,197,488 A | 3/1993 | Kovacevic |
| 5,360,016 A | 11/1994 | Kovacevic |
| 5,425,775 A | 6/1995 | Kovacevic |
| 5,470,354 A | 11/1995 | Hershberger et al. |
| 5,683,396 A | 11/1997 | Tokish et al. |
| 5,688,279 A | 11/1997 | McNulty et al. |
| 5,702,429 A | 12/1997 | King |
| 5,853,745 A | 12/1998 | Darouiche |
| 5,871,018 A | 2/1999 | Delp et al. |
| 5,921,929 A | 7/1999 | Goll et al. |
| 6,014,588 A | 1/2000 | Fitz |
| 6,063,091 A | 5/2000 | Lombardo et al. |
| 6,090,114 A | 7/2000 | Matsuno et al. |
| 6,228,089 B1 | 5/2001 | Wahrburg et al. |
| 6,245,109 B1 | 6/2001 | Mendes et al. |
| 6,493,588 B1 | 12/2002 | Malaney et al. |
| 6,505,075 B1 | 1/2003 | Weiner |
| 6,558,391 B2 | 5/2003 | Axelson, Jr. et al. |
| 6,573,706 B2 | 6/2003 | Mendes et al. |
| 6,583,630 B2 | 6/2003 | Mendes et al. |
| 6,621,278 B2 | 9/2003 | Ariav |
| 6,645,214 B2 | 11/2003 | Brown |
| 6,701,174 B1 | 3/2004 | Krause et al. |
| 6,758,850 B2 | 7/2004 | Smith et al. |
| 6,821,299 B2 | 11/2004 | Kirking et al. |
| 6,856,141 B2 | 2/2005 | Ariav |
| 6,920,347 B2 | 7/2005 | Simon et al. |
| 6,925,339 B2 | 8/2005 | Grimm et al. |
| 6,984,993 B2 | 1/2006 | Ariav |
| 7,018,416 B2 | 3/2006 | Hanson et al. |
| 7,022,141 B2 | 4/2006 | Dwyer et al. |
| 7,029,477 B2 | 4/2006 | Grimm |
| 7,080,554 B2 | 7/2006 | Ariav |
| 7,156,853 B2 | 1/2007 | Muratsu |
| 7,190,273 B2 | 3/2007 | Liao et al. |
| 7,195,645 B2 | 3/2007 | Disilvestro et al. |
| 7,206,627 B2 | 4/2007 | Abovitz et al. |

(Continued)

*Primary Examiner* — Sameh Boles
(74) *Attorney, Agent, or Firm* — Mayback & Hoffman, P.A.; Gregory L. Mayback; Thomas Bethea

(57) ABSTRACT

A method for detecting biometric parameters includes the steps of performing a bone graft procedure on a hip, providing a biometric sensor at the hip, and measuring a biometric parameter at the hip with the sensor. The sensor is capable of measuring parameters in an adjacent surrounding including pressure, tension, shear, relative position, and vascular flow. Data relating to the biometric parameter is transmitted to an external source and the data are analyzed to evaluate a biometric condition of the hip. A set of the sensors can be placed on the hip.

12 Claims, 14 Drawing Sheets

U.S. PATENT DOCUMENTS

| | | |
|---|---|---|
| 7,266,989 B2 | 9/2007 | Ariav |
| 7,313,491 B2 | 12/2007 | Ariav |
| 7,325,460 B2 | 2/2008 | Ariav |
| 7,366,562 B2 | 4/2008 | Dukesherer et al. |
| 7,442,196 B2 | 10/2008 | Fisher et al. |
| 7,458,977 B2 | 12/2008 | McGinley et al. |
| 7,488,324 B1 | 2/2009 | Metzger et al. |
| 7,520,179 B2 | 4/2009 | Bernstein |
| 7,522,701 B2 | 4/2009 | Jensen et al. |
| 7,525,309 B2 | 4/2009 | Sherman et al. |
| 7,527,632 B2 | 5/2009 | Houghton |
| 7,533,571 B2 | 5/2009 | Ariav |
| 7,542,791 B2 | 6/2009 | Mire et al. |
| 7,547,307 B2 | 6/2009 | Carson et al. |
| 7,578,821 B2 | 8/2009 | Fisher et al. |
| 7,606,613 B2 | 10/2009 | Simon et al. |
| 7,710,124 B2 | 5/2010 | Ariav |
| 7,716,988 B2 | 5/2010 | Ariav |
| 2002/0029784 A1 | 3/2002 | Stark |
| 2004/0054302 A1 | 3/2004 | Czernicki |
| 2004/0127793 A1 * | 7/2004 | Mendlein et al. ............. 600/442 |
| 2005/0012610 A1 | 1/2005 | Liao et al. |
| 2005/0015002 A1 * | 1/2005 | Dixon et al. ................... 600/407 |
| 2005/0020941 A1 | 1/2005 | Tarabichi |
| 2005/0176823 A1 | 8/2005 | Diaz |
| 2005/0273170 A1 | 12/2005 | Navarro et al. |
| 2006/0004431 A1 | 1/2006 | Fuller |
| 2006/0036324 A1 * | 2/2006 | Sachs et al. ................. 623/17.11 |
| 2006/0058798 A1 | 3/2006 | Roman |
| 2006/0093646 A1 | 5/2006 | Cima |
| 2006/0204738 A1 | 9/2006 | Dubrow |
| 2006/0232408 A1 | 10/2006 | Nycz |
| 2006/0246208 A1 | 11/2006 | Darouiche |
| 2006/0271112 A1 | 11/2006 | Martinson |
| 2007/0134287 A1 | 6/2007 | Troxel |
| 2007/0219561 A1 | 9/2007 | Lavallee |
| 2007/0272747 A1 | 11/2007 | Woods |
| 2008/0287856 A1 | 11/2008 | MacDonald |
| 2008/0300481 A1 | 12/2008 | Groszmann |
| 2008/0312530 A1 | 12/2008 | Malackowski |
| 2009/0000627 A1 | 1/2009 | Quaid |
| 2009/0105557 A1 | 4/2009 | Najafi |
| 2009/0187120 A1 | 7/2009 | Nycz |

* cited by examiner

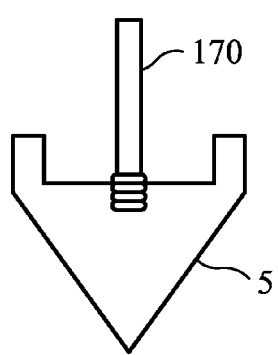
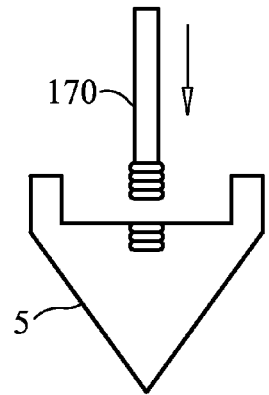
FIG. 19          FIG. 20
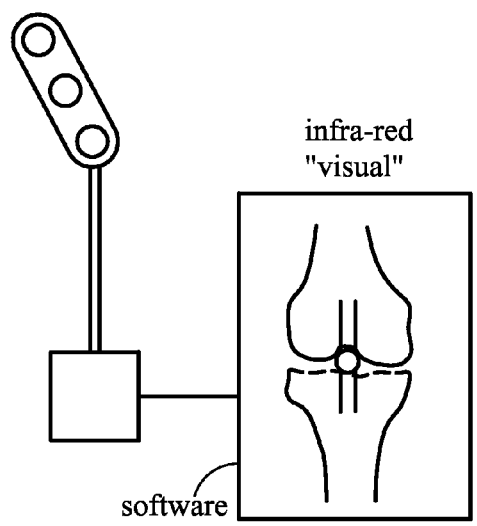
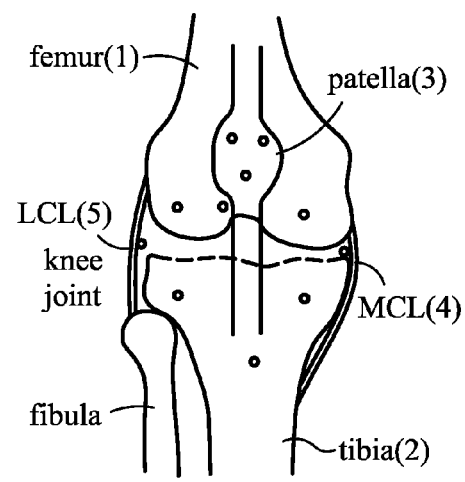
FIG. 21          FIG. 23 ligament sensors
sensor clamp

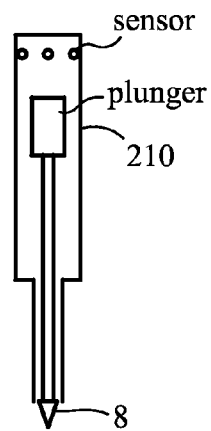
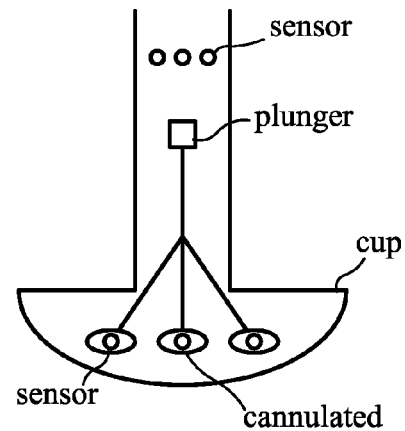
FIG. 34　　　　　　FIG. 35
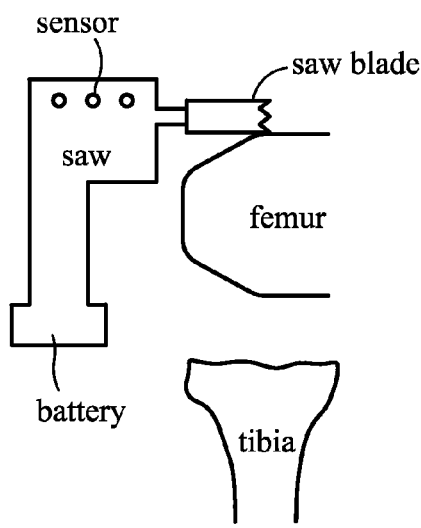
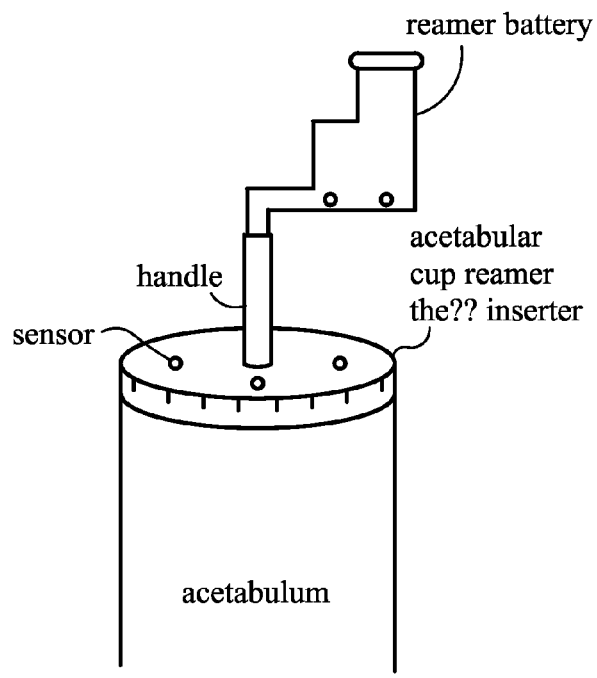
FIG. 36　　　　　　FIG. 37

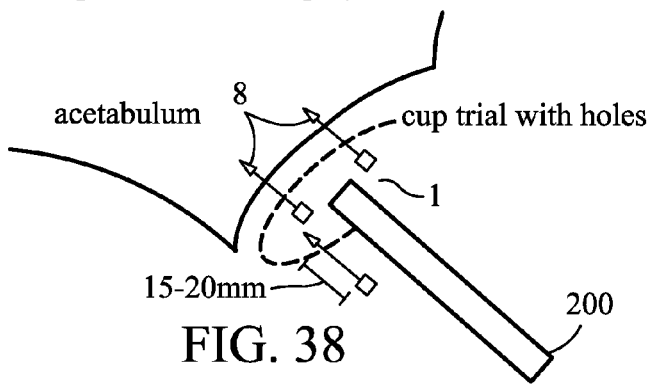
FIG. 38
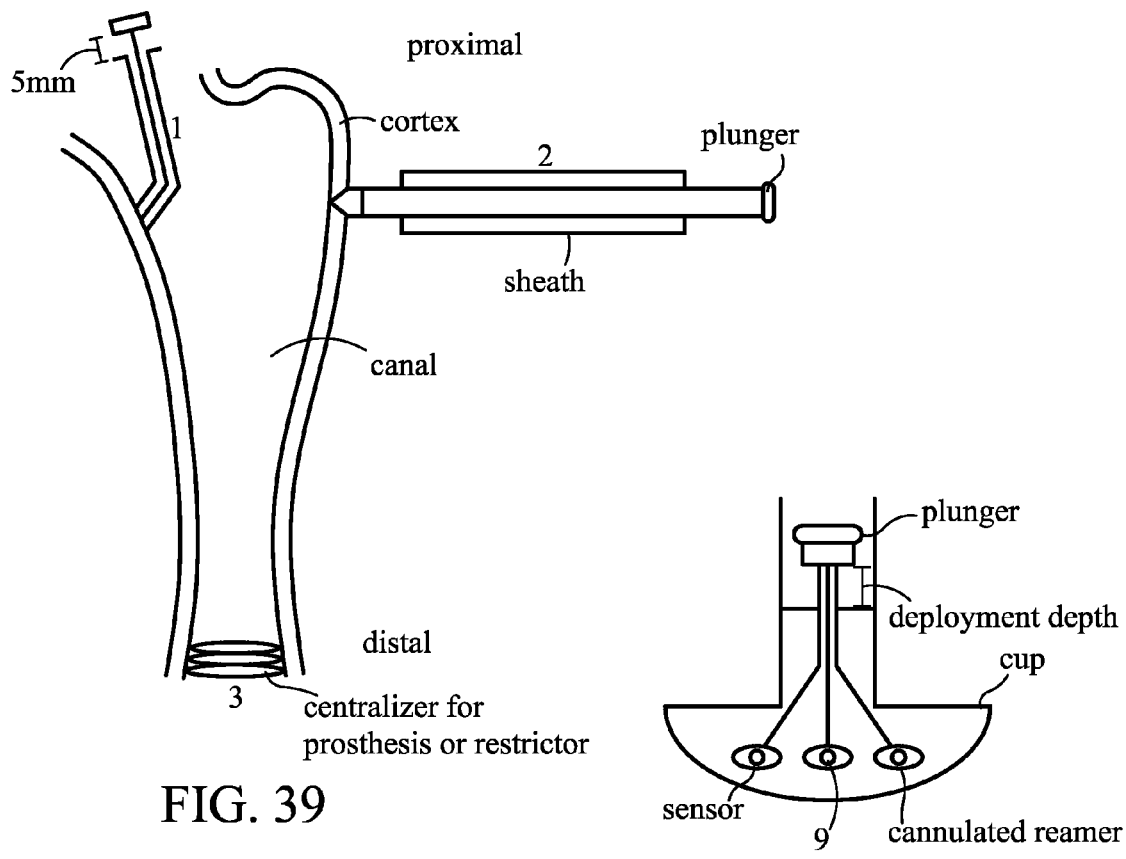
FIG. 39
FIG. 40

METHOD FOR DETECTING BODY PARAMETERS

CROSS-REFERENCE TO RELATED APPLICATION

This application is a divisional of U.S. patent application Ser. No. 11/391,988, filed on Mar. 29, 2006, now U.S. Pat. No. 7,918,887, which claims priority, under 35 U.S.C. §119, of U.S. Provisional Application No. 60/665,797, filed Mar. 29, 2005, and U.S. Provisional Application Nos. 60/763,761 and 60/763,869, both filed Feb. 1, 2006.

FIELD OF THE INVENTION

The present invention lies in the field of medical devices, in particular, in the field of externally applied and embedded sensor systems for detecting specific parameters of a physiological (e.g., musculoskeletal) system and determining the exact anatomic site of activity, and methods for detecting parameters of anatomical sites.

BACKGROUND OF THE INVENTION

Sensor technology has been disclosed in U.S. Pat. Nos. 6,621,278, 6,856,141, and 6,984,993 to Ariav and assigned to Nexense Ltd. (the "Nexense patents").

It would be beneficial to apply existing sensor technology to biometric data sensing applications so that health care personnel can determine characteristics of anatomic sites.

BRIEF SUMMARY OF THE INVENTION

It is accordingly an object of the present invention to provide a sensor system that can detect specific parameters (e.g., of a musculoskeletal system) and determine the exact anatomic site of activity and methods for detecting parameters of anatomical sites that overcome the hereinafore-mentioned disadvantages of the heretofore-known devices and methods of this general type and that provides an externally applied and/or embedded sensor to give healthcare providers real time information regarding their patients. The information can include pathological processes as well as information regarding surgical procedures and implanted devices. The sensors can be activated by internal or external mechanisms, and the information relayed through wireless pathways. The sensor system will allow early intervention or modification of an implant system and can use existing sensors. For example, the sensors disclosed in Nexense patents can be used.

With the foregoing and other objects in view, there is provided, in accordance with the invention, a method for detecting biometric parameters including the steps of performing a surgical procedure on at least one hip, implanting at least one biometric transceiver at the at least one hip, transmitting a first energy wave from the transceiver into a procedure area including at least one of the hip and an area adjacent the hip, quantitatively assessing the behavior of the energy wave with the transceiver, after transmitting the first energy wave: transmitting a second energy wave from the transceiver into the procedure area; and quantitatively assessing the behavior of the second energy wave. At least one of the first and second energy waves are pulsed during transmission in a vibratory manner to stimulate the procedure area in accordance with at least one detected parameter of the procedure area. A current status is determined of the at least one parameter of the procedure area selected from the group consisting of pressure, tension, shear, relative position, bone density, fluid viscosity, temperature, strain, angular deformity, vibration, venous flow, lymphatic flow, load, torque, distance, tilt, shape, elasticity, motion, bearing wear, subsidence, bone integration, change in viscosity, particulate matter, kinematics, stability, and vascular flow with the transceiver based upon a comparison between the assessed behavior of the first and second energy waves.

In accordance with another mode of the invention, there are provided the steps of transmitting data relating to the at least one biometric parameter to an external source and analyzing the data to evaluate a biometric condition of the at least one hip.

In accordance with a further mode of the invention, a set of the transceivers is provided on the at least one hip.

In accordance with an added mode of the invention, based upon the evaluation of the biometric condition of the at least one hip, a currently ongoing interoperative procedure at the procedure area is changed.

In accordance with an additional mode of the invention, based upon the evaluation of the biometric condition of the at least one hip, the anatomic condition relating to the procedure area is chronically monitored.

In accordance with yet another mode of the invention, energy is provided from outside the procedure area to the transceiver to power the transceiver and, thereby, create the energy wave and quantitatively assess the behavior of the energy wave.

In accordance with yet a further mode of the invention, the energy is provided through at least one of an electromagnetic couple, a magnetic couple, a capacitive couple, an inductive couple, a sonic couple, an ultrasonic couple, a fiber optic couple, an optical couple, and an infrared couple.

In accordance with yet an added mode of the invention, a set of the biometric transceivers is provided at the procedure area, an energy wave is transmitted from the transceivers into the procedure area, the behavior of the energy wave is quantitatively assessed with at least one of the transceivers, and, based upon the assessed behavior, a current status of the at least one parameter is determined.

In accordance with yet an additional mode of the invention, a set of the biometric transceivers is provided at the procedure area, energy waves are transmitted from the transceivers into the procedure area, the behaviors of the energy waves are quantitatively assessed with the transceivers, and, based upon the assessed behaviors, a current status of the at least one parameter is determined.

In accordance with again another mode of the invention, the area adjacent the hip is a second bone different from the hip, and an energy wave is transmitted from the transceiver, into the second bone, and back to the transceiver.

In accordance with again a further mode of the invention, the status determining step is carried out by determining a current status of at least two of the group of parameters with the transceiver.

In accordance with a concomitant mode of the invention, the at least one biometric transceiver is embedded at the at least one hip.

Other features that are considered as characteristic for the invention are set forth in the appended claims.

Although the invention is illustrated and described herein as embodied in a sensor system that can detect specific body parameters and determine exact anatomic site of activity and methods for detection, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments the present invention will be apparent from the following detailed description of the preferred embodiments thereof, which description should be considered in conjunction with the accompanying drawings in which:

FIG. 19 is a diagrammatic, enlarged, cross-sectional view of a handle connected to an implantable sensor body according to the invention;

FIG. 20 is a diagrammatic, enlarged, cross-sectional view of the handle of FIG. 19 disconnected from the sensor body;

FIG. 21 is a diagrammatic illustration of an infra-red visualization system;

FIG. 23 is a fragmentary, partially hidden, anterior view of a knee joint;

FIG. 34 is a fragmentary, cross-sectional view of a trocar tip according to the invention housing sensor elements;

FIG. 35 is fragmentary, cross-sectional view of an inserter for an array of sensors;

FIG. 36 is diagrammatic, side devotional view of a cutter housing an array of sensors according to the invention;

FIG. 37 is a diagrammatic, side devotional view of a bone reamer;

FIG. 38 is a fragmentary, cross-sectional view of a sensor system according to the invention implanted in a hip;

FIG. 39 is a fragmentary, cross-sectional view of a sensor system according to the invention implanted in a femur;

FIG. 40 is a fragmentary, cross-sectional view of a cup sensor inserter according to the invention for deployment of multiple sensors;

DETAILED DESCRIPTION OF THE PREFERRED EMBODIMENTS

Figure 1:
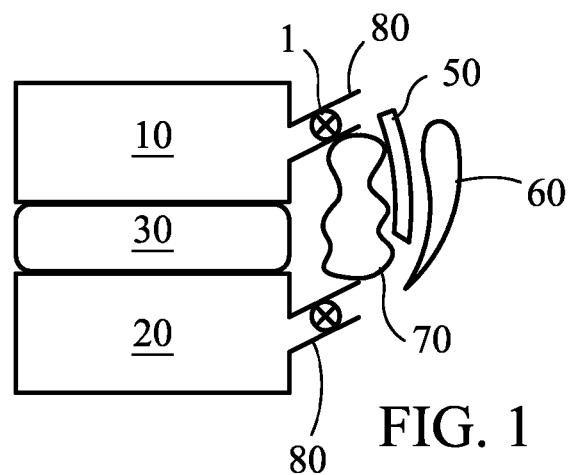
FIG. 1 is a diagrammatic, fragmentary, lateral view of a portion of a spine with a non-instrumented fusion of the spine and sensors according to the invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise.

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

An externally applied sensor system according to the present invention can be used to evaluate skin integrity and pathological pressure that can lead to skin ischemia and ultimately skin breakdown (Decubiti). It is important to detect certain parameters that can lead to skin breakdown. Elements such as pressure, time, shear, and vascular flow, for example, are important to detect. The specific anatomic location is needed.

The sensor system of the present invention can be embedded in a thin, adhesive, conforming material that is applied to specific areas of concern. Exemplary areas include the heel, hips, sacrum, and other areas of risk. These sensors map out the anatomic area. If threshold parameters are exceeded, the sensors inform a telemetric receiver that, in turn, activates an alarm to the nurse or other health care professional. In one specific application, the information is used to control the bed that the patient is lying upon to relieve the area of concern. In particular, adjustment of aircells in the mattress can be made to unload the affected area of concern.

The external sensor system can be configured in various ways. In an exemplary embodiment, a sensor is disposed within a thin, conformable adhesive that is applied directly to the patient's body and is powered by a thin lithium battery. This sensor(s) documents specific parameters such as pressure, time, shear, and vascular flow. The sensor telemetrically informs a receiving unit and sets an alarm if certain preprogrammed parameters are exceeded. In one embodiment where a visual aid is provided (such as a computer screen displaying the patient's body outline, the exact area of concern can be highlighted and, thereby, visualized by the health care professional.

Embedded sensors are needed to detect certain internal parameters that are not directly visible to the human eye. These sensors will be used in specific locations to detect specific parameters.

One way of embedding a sensor is through an open surgical procedure. During such a surgical procedure, the sensor is embedded by the surgeon directly into bone or soft tissue or is attached directly to a secured implant (e.g., a prosthesis (hip, knee)). The sensor system is used during the surgical procedure to inform the surgeon on the position and/or function of the implant and of soft tissue balance and/or alignment. The sensor is directly embedded with a penetrating instrument that releases the sensor at a predetermined depth. The sensor is attached to the secured implant with a specific locking system or adhesive. The sensor is activated prior to closure for validating the sensor.

Another way of embedding a sensor is through a percutaneous procedure. The ability to implant sensors in specific locations is important to evaluate internal systems. Sensors of varying diameters can be implanted into bone, soft tissue, and/or implants. The procedure is applied under visualization supplied, for example, by fluoroscopy, ultrasound imaging, and CAT scanning. Such a procedure can be performed under local or regional anesthesia. The parameters evaluated are as set forth herein. The percutaneous system includes a thin instrument with a sharp trocar that penetrates the necessary tissue plains and a deployment arm releases the sensor(s) at predetermined depth(s). The instrument could also house the necessary navigation system to determine the specific anatomic location required.

The parameters to be evaluated and time factors determine the energy source required for the embedded sensor. Short time frames (up to 5 years) allow the use of a battery. Longer duration needs suggest use of external activation or powering systems or the use of the patient's kinetic energy to supply energy to the sensor system. These activation systems can be presently utilized. The sensors would also be activated at predetermined times to monitor implant cycles, abnormal motion and implant wear thresholds.

Information is received telemetrically. In one exemplary embodiment, the sensors are preprogrammed to "activate" and send required information if a specific threshold is exceeded. The sensors could also be activated and used to relay information to an external receiver. Further applications allow readjustment of a "smart implant" to release specific medications, biologics, or other substances, or to readjust alignment or modularity of the implant.

The sensor system is initially activated and read in a doctor's office and further activation can occur in the patient's house, with the patient having ability to send the information through Internet applications, for example, to the physician.

Software will be programmed to receive the information, process it, and, then, relay it to the healthcare provider.

The sensor system of the present invention has many different applications. For example, it can be used to treat osteoporosis. Osteoporosis is a pathological condition of bone that is characterized by decreased bone mass and increased risk of fracture. It is well accepted that bone-mineral content and bone-mineral density are associated with bone strength.

Bone density is an extremely important parameter of the musculoskeletal system to evaluate. Bone density measurements are used to quantify a person's bone strength and ultimately predict the increased risks associated with osteoporosis. Bone loss leads to fractures, spinal compression, and implant loosening. Presently, physicians use external methods such as specialized X-rays.

The unit of measurement for bone densitometry is bone-mineral content, expressed in grams. Bone density changes are important in the evaluation of osteoporosis, bone heating, and implant loosening from stress shielding. Another important evaluation is in regard to osteolysis. Osteolysis can destroy bone in a silent manner. It is a pathological reaction of the host to bearing wear, such as polyethylene. The polyethylene particles activate an immune granulomatous response that initially affects the bone surrounding the implant. Bone density changes will occur prior to cystic changes that lead to severe bone loss and implant failure.

There are multiple external systems that can evaluate bone density. The problems with such systems encountered are related to the various systems themselves, but also to the socio-economic constraints of getting the patient into the office to evaluate a painless disease; coupled with the constricted payment allocations that cause long intervals between evaluations.

Sensors used according to the present invention allow evaluation of changes in bone density, enabling health care providers to know real time internal data. Application of the sensors can assess osteoporosis and its progression and/or response to treatment. By evaluating changes in bone density, the sensors provide early information regarding fracture healing and early changes of osteolysis (bone changes relating to polyethylene wear in implants).

Although the instrumentation various with different modalities, all record the attenuation of a beam of energy as it passes through bone and soft tissue. Comparisons of results are necessarily limited to bones of equal shape, which assumes a constant relationship between the thickness of the bone and the area that is scanned. Moreover, the measurements are strictly skeletal-site-specific; thus, individuals can be compared only when identical locations in the skeleton are studied.

Dual-energy x-ray absorptiometry can be used to detect small changes in bone-mineral content at multiple anatomical sites. A major disadvantage of the technique is that it does not enable the examiner to differentiate between cortical and trabecular bone. Quantitative ultrasound, in contrast to other bone-densitometry methods that measure only bone-mineral content, can measure additional properties of bone such as mechanical integrity. Propagation of the ultrasound wave through bone is affected by bone mass, bone architecture, and the directionality of loading. Quantitative ultrasound measurements as measures for assessing the strength and stiffness of bone are based on the processing of the received ultrasound signals. The speed of sound and the ultrasound wave propagates through the bone and the soft tissue. Prosthetic loosening or subsidence, and fracture of the femur/tibia/acetabulum or the prosthesis, are associated with bone loss. Consequently, an accurate assessment of progressive quantifiable changes in periprosthetic bone-mineral content may help the treating surgeon to determine when to intervene in order to preserve bone stock for revision arthroplasty. This information helps in the development of implants for osteoporotic bone, and aids in the evaluation of medical treatment of osteoporoses and the effects of different implant coatings.

The sensor system of the present invention can be used to evaluate function of internal implants. Present knowledge of actual implant function is poor. Physicians continue to use external methods, including X-rays, bone scans, and patient evaluation. However, they are typically left only with open surgical exploration for actual investigation of function. Using sensors according to the present invention permits detection of an implant's early malfunction and impending catastrophic failure. As such, early intervention is made possible. This, in turn, decreases a patient's morbidity, decreases future medical care cost, and increases the patient's quality of life.

The sensors can be attached directly to implant surfaces (pre-operatively and/or intra-operatively) and/or directly to the implant-bone interface. Sensors can be implanted into the bone and soft tissue as well. In such an application, the physician could evaluate important parameters of the implant-host system. Exemplary parameters that could be measured include: implant stability, implant motion, implant wear, implant cycle times, implant identification, implant pressure/load, implant integration, joint fluid analysis, articulating surfaces information, ligament function, and many more.

Application of sensors according to the invention allows one to determine if the implant is unstable and/or if excessive motion or subsidence occurs. In an exemplary application, the sensor can be configured to release an orthobiologic from an activated implanted module to increase integration. Alternatively and/or additionally, the implant system with the sensors can be used to adjust the angle/offset/soft tissue tension to stabilize the implant if needed.

Sensors can be used to detect whether or not implant bearings are wearing out. Detectable bearing parameters include early wear, increased friction, etc. An early alarm warning from the sensor could enable early bearing exchange prior to catastrophic failure.

A joint implant sensor can detect an increase in heat, acid, or other physical property. Such knowledge would provide the physician with an early infection warning. In an exemplary infection treatment application, the sensor can activate a embedded module that releases an antibiotic.

The sensors can be used to analyze knee surgeries. Such sensors can be placed posteriorly in the knee to evaluate popliteal artery flow, pressure, and/or rhythm. A femoral implant sensor is placed anteriorly to monitor femoral artery/venous flow, pressure, and/or rhythm. An internal vascular monitor can be part of the implant and include devices to release antihypertensive or anti-arrthymic modules to modify vascular changes when needed.

In one embodiment, the internal orthopedic implant is, itself, the sensor of the present invention. In a trauma situation, for example, the reduction screw can be both the implant and the sensor. Such a screw can detect abnormal motion at the fracture site and confirm increase in density (i.e., healing). Such an application allows percutaneous implantation of bone morphogenic protein (BMP) to aid in healing or a percutaneous adjustment of the hardware.

The sensor of the present invention can be used in spinal implants. A sensor placed in the spine/vertebrae can detect abnormal motion at a fusion site. The sensor evaluates spinal implant integration at the adjacent vertebral segments and/or detects adjacent vertebral segment instability. Implanted sensors can activate a transitioning stabilizing system or implant and determine the areas of excessive motion to enable percutaneous stability from hardware or an orthobiologic. Referring now to the figures of the drawings in detail and first, particularly to FIG. 1 thereof, there is shown a fragmentary lateral view of a fusion of a portion of the spine. An upper vertebra 10 is separated from a lower vertebra 20 by a disc 30. A bone graft 40 is covered first by an inferior facet 50 and second by a superior facet 60. FIG. 2 is an anterior-posterior view of the spine portion of FIG. 1 in which the bone graft 40 is shown on either side of the disc 30 with opposing transverse processes 70. Sensors 1 according to the present invention can detect and transmit information regarding motion and loads of the vertebra 10, 20 and are implanted in various spinal elements. The elements can include the spinal pedicles 80, transverse processes 70, facets, etc.

Figure 2:
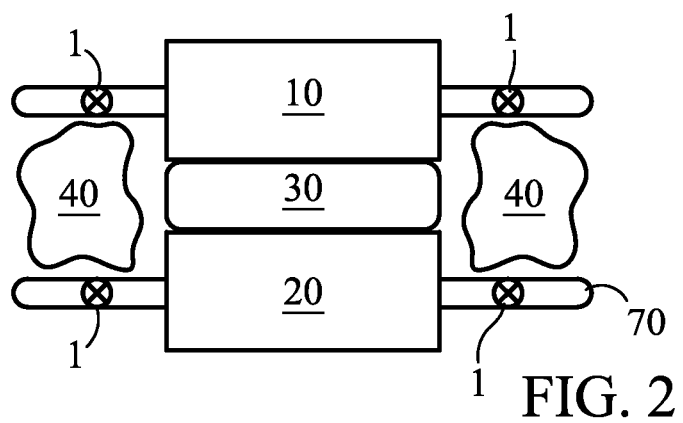
FIG. 2 is a diagrammatic, fragmentary, anterior-posterior view of the spine portion of FIG. 1.

FIGS. 1 and 2 depict how sensors 1 of the present invention can be used in non-instrumented fusions of the spine. The sensors 1 are activated at variable times in the post-operative period. Abnormal or excessive motion around the fusion "mass" helps detect a non-union, for example.

Figure 3:
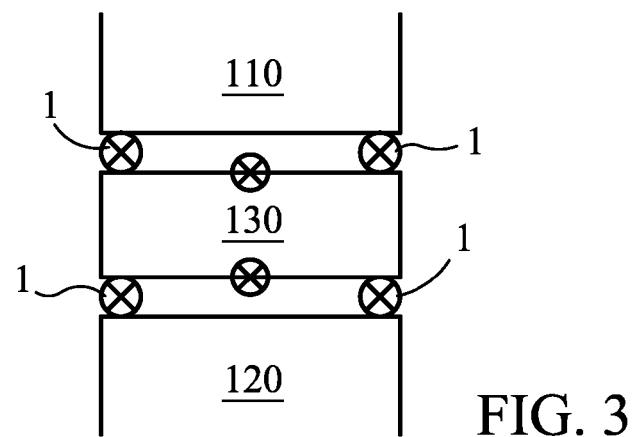
FIG. 3 is a diagrammatic, fragmentary, lateral view of a portion of a spine with an intervertebral cage and sensors according to the invention.

FIG. 3 depicts how sensors 1 of the present invention can be use in instrumented spinal fusions. More particularly, the sensors 1 are incorporated into the "cage" instrumentation 130 in between an inferior vertebral plate 110 and a superior vertebral plate 120. Such a sensor 1 detects motion and load and is activated to transmit information in the post-operative period to help determine if the fusion mass was solid.

Figure 4:
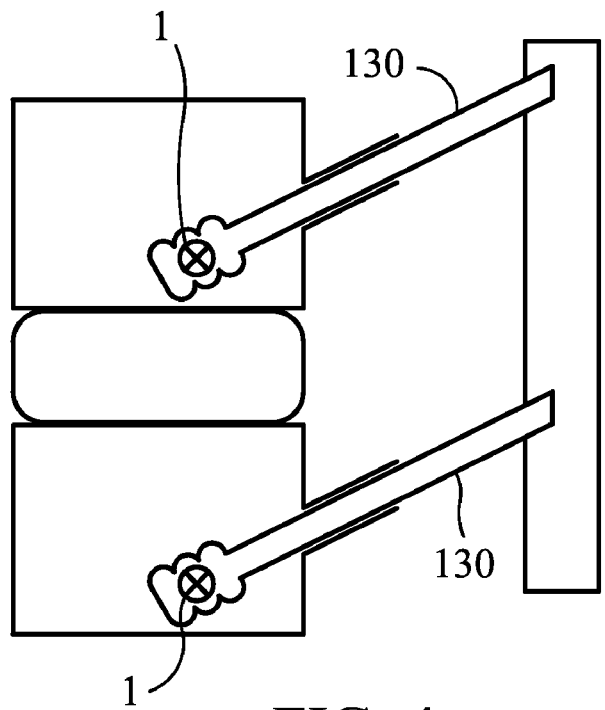
FIG. 4 is a diagrammatic, fragmentary, anterior-posterior view of the spine portion of FIG. 1 with sensors according to the invention in pedical screws

FIG. 4 depicts how sensors 1 of the present invention can be use in pedicle screws 130. More particularly, sensors 1 are incorporated into the pedicle screw 130 to help detect any abnormal motion between vertebrae in the fusion mass.

Figure 5:
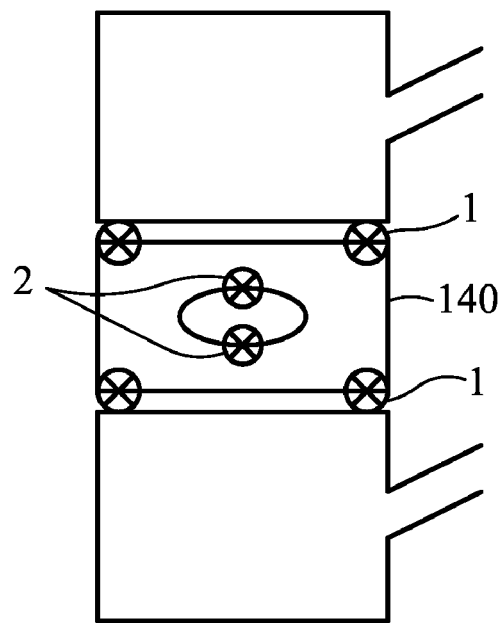
FIG. 5 is a diagrammatic, fragmentary, lateral view of a portion of a spine with an intervertebral disc implant and sensors according to the invention.

FIG. 5 depicts how sensors 1 of the present invention can be use in invertebral disc implants (replacements). More particularly, an artificial disc replacement 140 has sensors 1 placed on the metal-bone interface, for example. These sensors 1 detect loads as well as motion to help, intra-operatively, in the placement of the disc 140 and, post-operatively, determine stable integration of the disc-bone interface. Internal sensors 2 detect "normal" motion between the articulating disc internal interfaces to help confirm, post-operatively, that the disc replacement is functioning and optimize levels with variable loads and spinal motion.

Figure 6:
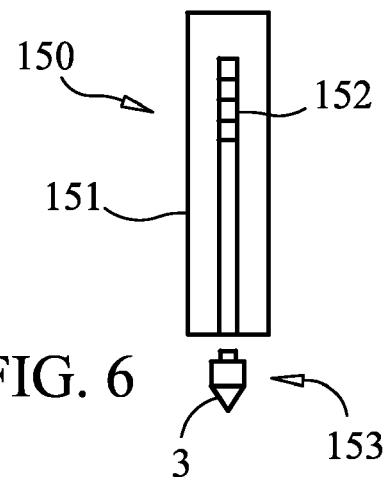
FIG. 6 is a diagrammatic, fragmentary, enlarged cross-sectional view of a sensor inserting instrument according to the invention.
Figure 7:
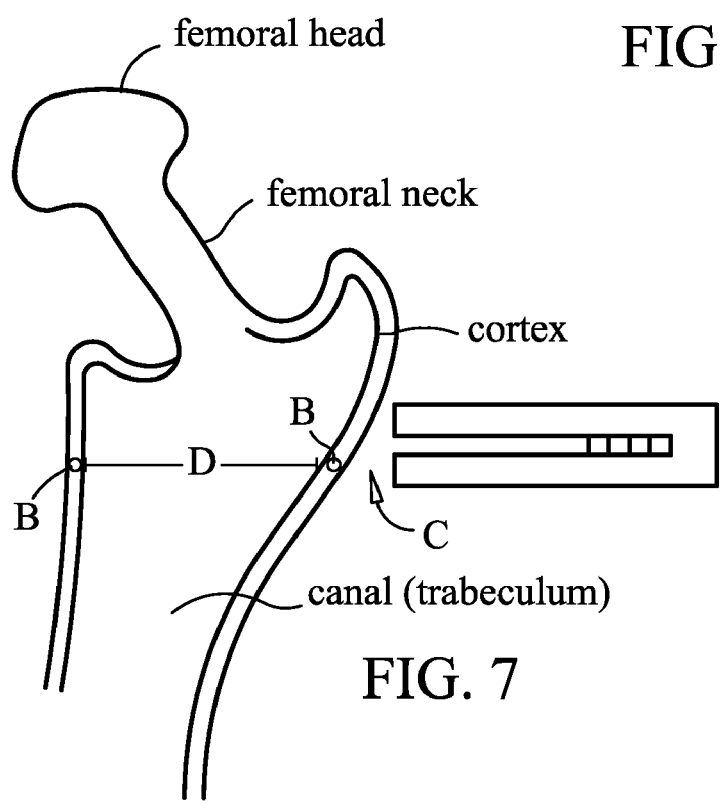
FIG. 7 is a diagrammatic, fragmentary cross-sectional view of an upper femur with sensors according to the invention implanted with the instrument of FIG. 6.
Figure 8:
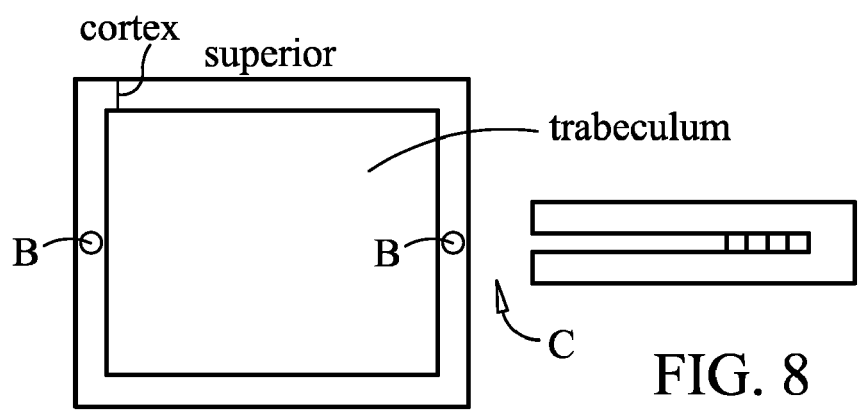
FIG. 8 is a diagrammatic, fragmentary cross-sectional view of a vertebra with sensors according to the invention implanted with the instrument of FIG. 6.

FIG. 6 depicts a sensor deploying instrument 150 is depicted as having a handle 151 and a plunger 152. The handle 151 and plunger 152 allow the insertion of the sensor 3 that is part of a trocar 153. The trocar 153 can penetrate the cortex and the sensor 3 can be deployed. FIG. 7 depicts the insertion of the sensor 3 in the femur and FIG. 8 depicts the insertion of the sensor 3 in a vertebra. The sensor 3 can, then, be decoupled with a coupling mechanism 154, for example, by an unscrewing or a derotating process. These body areas are used as examples because they are the most commonly affected area with regard to osteoporosis and trauma relating to osteoporosis. The sensor 3 can vary in size from several millimeters to over a centimeter. The sensor 3 can be implanted percutaneously or in an open surgical manner.

The sensor 3 can be part of hardware used in the hip and/or the spine. The sensor 3 can be placed at various depths to allow evaluation of the cortex as well as the travecular bone. With two deployed sensors 3, the distance between the sensors 3 can be determined at the area of concern and the power field that can be generated. The energy fields can be standard energy sources such as ultrasound, radiofrequency, and/or electromagnetic fields. The deflection of the energy wave over time, for example, will allow the detection of changes in the desired parameter that is being evaluated.

An exemplary external monitoring sensor system according to FIGS. 6 to 8 enables on-contact nightly reads on bone mineral content and density. The sensor system can also enables a transfer of energy waves in a vibratory pattern that can mimic load on the bone and lead to improved bone mineral content and density. The sensors can also send energy waves through or across an implant to, thus, aid in healing of a fracture.

Figure 9:
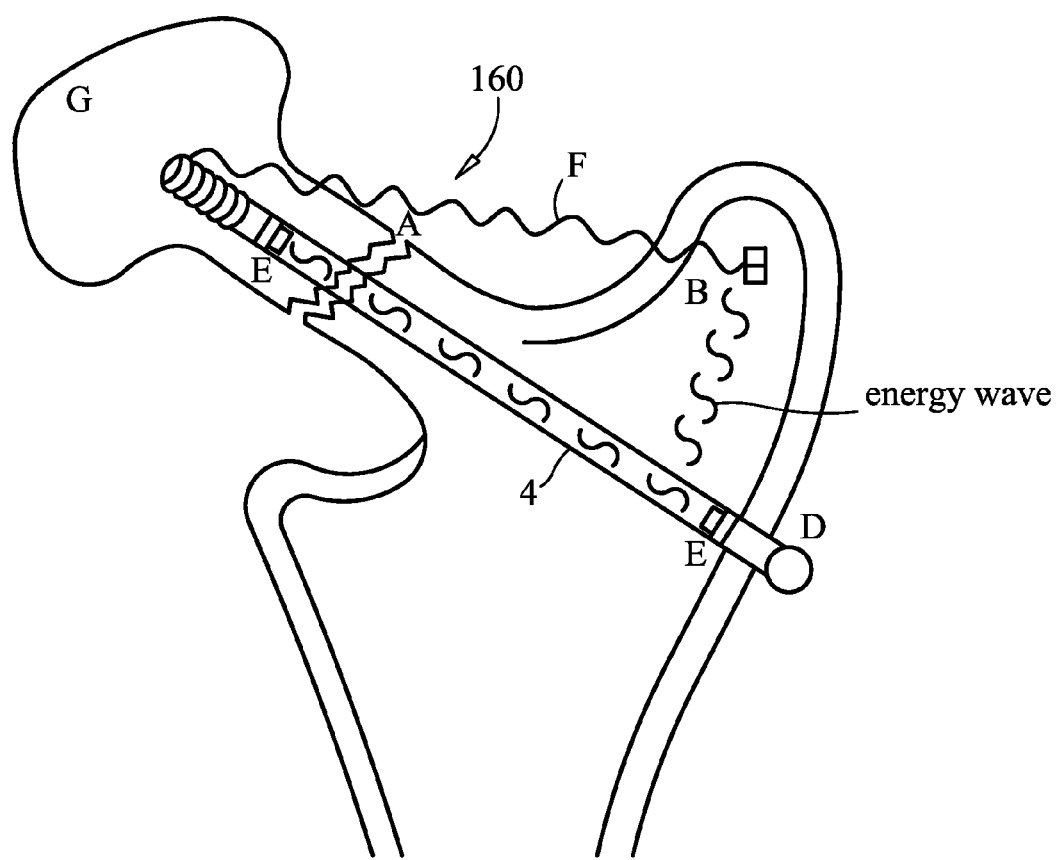
FIG. 9 is a diagrammatic, fragmentary cross-sectional view of a femur with sensors in a screw according to the invention.

Fracturing of a hip and a spinal vertebra is common with respect to osteoporosis and trauma. FIG. 9 depicts the use of a screw 4 as the internal sensor. The fracture 160 is spanned by a compression screw 4 and the sensors 4 are embedded in the screw 4. The sensors 4 in the screw 4 can send energy across the fracture site to obtain a baseline density reading and monitor the change in density over time to confirm healing. The sensors 4 can also be activated externally to send energy waves to the fracture itself to aid in healing. The sensors 4 can also detect the change in motion at the fracture site as well as the motion between the screw and bone. Such information aids in monitoring healing and gives the healthcare provider an ability to adjust weight bearing as indicated. Once the fracture is healed, the sensors 4 shown in FIGS. 10 and 11 within the greater trochanter can now be activated to send energy waves to the other two sensors 4. This will enable continued evaluation of bone density. The sensors 4 can be activated with a sensor bed system when the patient is asleep, for example. The energy source and receiver can be attached to the bed undersurface, for example. The received information can be evaluated every night if needed and sent by standard telephonic measures to the doctor. The activation of the sensors at night will enable specific interval readings during treatment of osteoporosis by various medications.

External and internal energy waves sent with sensors according to the invention can be used during the treatment of fractures and spinal fusions.

Figure 10:
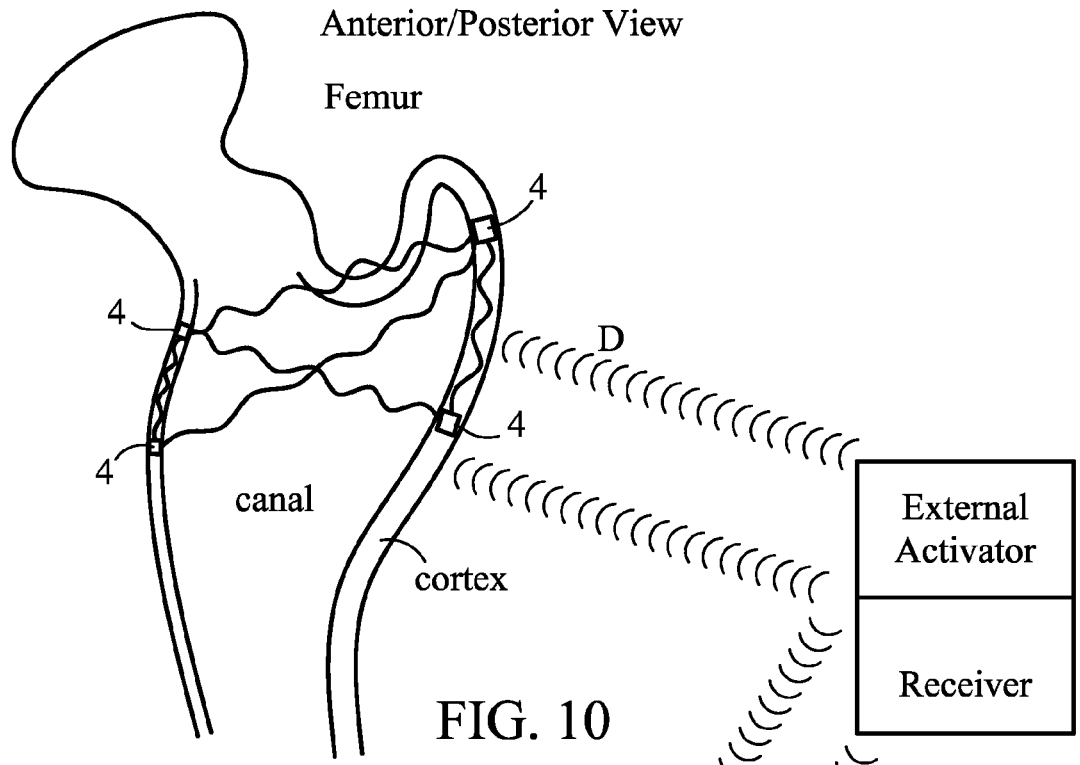
FIG. 10 is a diagrammatic, fragmentary cross-sectional view of a femur with implanted sensors according to the invention.
Figure 11:
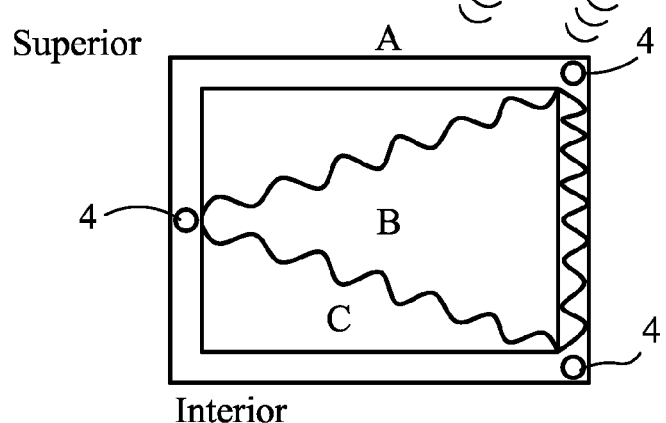
FIG. 11 is a diagrammatic, fragmentary cross-sectional view of a vertebra with sensors according to the invention.

The use of ultrasound, pulsed electromagnetic fields, combined magnetic fields, capacitive coupling, and direct electrical current have been studied in their effects on the up regulation of growth factors. Pulsed Ultrasound has shown to activate "integrins," which are receptors on cell surfaces that, when activated, produce an intracellular cascade. Proteins involved in inflammation, angiogenesis, and bone healing are expressed. These proteins include bone morphogenic protein (BMP)-7, alkaline phosphatase, vascular endothelial growth factor and insulin growth factor (IGF)-1. The use of pulsed electromagnetic fields have shown increased bone healing times in animals. Various waveforms affect the bone in different ways, A sensor system using quantitative ultrasound can be used to evaluate calcaneal bone density externally. The system according to the invention is attached to the patients' bed and, by using external ultrasound wave forms as shown in FIGS. 10 and 11, the bone density can be evaluated. The use of energy fields have been shown to stimulate the bone healing process. Stimulation an be effected with external measures, but use of internal sensor systems can change the waveforms and generate a vibratory signal that can effectively "load" the bone. This affect is known, by several orthopedic laws, to strengthen the bone cortex and effectively be use in the treatment of fractures and osteoporoses and is depicted in FIG. 10. The sensors in FIG. 10 are in the cortex or canal. The energy wave forms are sent to each other. They can be activated and received by an external system or be part of the sensor itself. Similarly, FIG. 11 depicts a vertebral segment in which sensors 4 send energy wave forms to each other and to an external receiver. Such a system/treatment can be used to treat fractures and osteoporosis.

The sensor system according to the present invention depicts mainly the hip and spine, but can be applied to all skeletal segments of the body. FIGS. 12 to 18 depict various orientations of sensors according to the invention for treating the knee, hip, and vertebrae.

FIGS. 19 and 20 depict one exemplary embodiment of a handle 170 that can be releasably connected to an implantable sensor body 5. In this embodiment, the handle has an exterior thread that screws into an interior correspondingly threaded bore of the body 5.

Sensors according to the invention are used in multiple orthopedic applications, including intra-operative joint implant alignment. Sensors and monitoring devices/systems that can be used include any of those well known in the art, such as those described in the Nexense patents. Computer assisted surgery is also commonplace.

Presently, the use of pins in the femur and tibia, allow arrays to be attached to the bones. Such attachment helps in spatial orientation of the knee/hip joint during the operation. These arrays are recognized by infrared optics or by electromagnetic devices (see FIGS. 21 and 22) to replay the information into a recognized software system that allows the surgeon to visualize the joint in a three-dimensional manner while overlaying the implant of choice on the bones. Problems encountered with the application of such pins are many:
  the need to penetrate bones outside the field of surgery;
  post-op pain and drainage from the pin sites;
  the possibility of pin loosening during the surgery as well as blocking the arrays and infra-red light;
  the pins require the surgeons to change the present positioning during the procedure, which can be difficult; and the electromagnetic field can be affected by various metals and instruments that are used in the surgery.

The time associated with inserting the pins, locking the arrays, registering the joint topography contributes to a significantly long procedure duration. There is still a need to individually touch multiple points on the femur and tibia to allow the computer to visualize the topography of the knee. The time for transmission of information from the sensors to the receiver also causes a potential delay. Therefore, it would be desireable to reduce or eliminate each of these problems.

Methods according to the invention include implanting the sensors in the field of surgery, using the sensors during surgery, and using the implanted sensors post-operatively to evaluate various desired parameters.

Figures 22, 24:
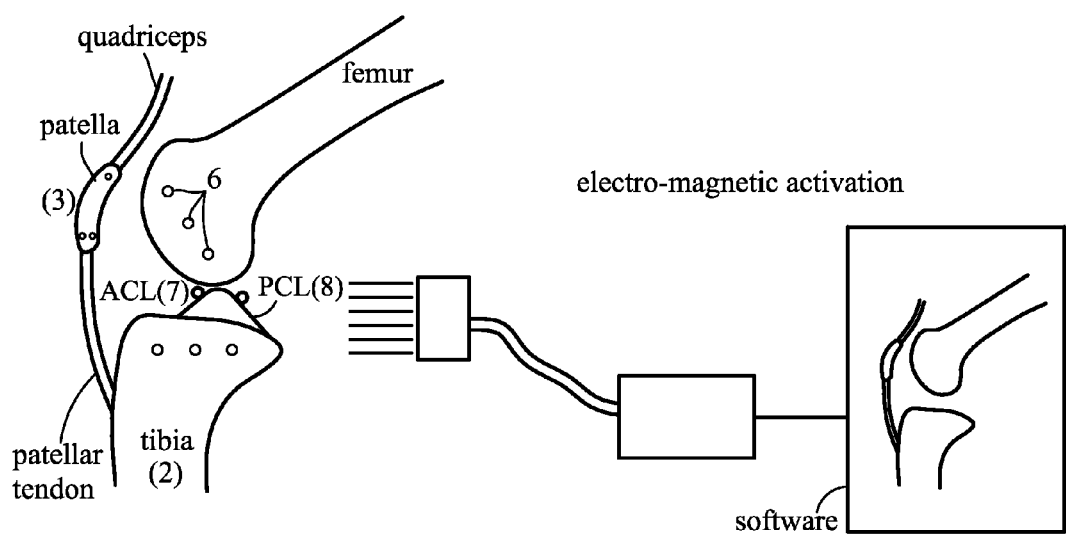
FIG. 22 is a diagrammatic illustration of an electromagnetic visualization system.
FIG. 24 is a fragmentary, partially hidden, lateral view of the knee joint.
Figure 25:
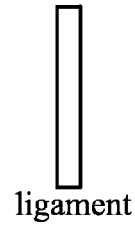
FIG. 25 is a fragmentary side elevational view of a ligament.
Figure 26:
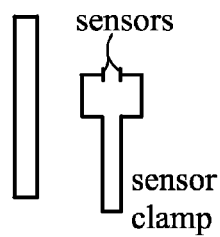
FIG. 26 is a fragmentary side elevational view of the ligament of FIG. 25 with a ligament sensor clamp according to the invention.
Figure 27:
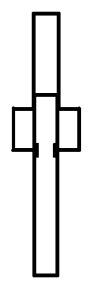
FIG. 27 is a fragmentary side elevational view of the ligament and ligament sensor clamp of FIG. 26.
Figure 28:
FIG. 28 is a fragmentary side elevational view of the ligament of FIG. 25 with sensors according to the invention attached thereto.

FIG. 23 illustrates embedded sensors 6 in the femur and the tibia, and FIG. 24 illustrates sensors 6 in the patella. The ligaments shown include the medial collateral ligament, the lateral collateral ligament, the anterior cruciate ligament, and the posterior cruciate ligament. The sensors 6 are implanted prior to surgery in percutaneously and/or arthroscopically or intra-operatively through open surgery. FIG. 25 depicts a ligament or tendon, FIG. 26 depicts a sensor clamp with a compressive and release handle, FIG. 27 depicts the deployment of the sensor and FIG. 28 reveals the deployed sensors in the ligament. As shown in the steps depicted by FIGS. 25 to 28, the sensors can be embedded into the ligaments (FIG. 25 illustrates an exemplary ligament) by providing a sensor clamp (FIG. 26) that is placed around the ligament (FIG. 27) and secures the sensors thereto as shown in FIG. 28. They can also be embedded into bone as shown later in FIG. 33. Standard radiograph techniques could be used to guide deployment angle and depth.

Figure 17:
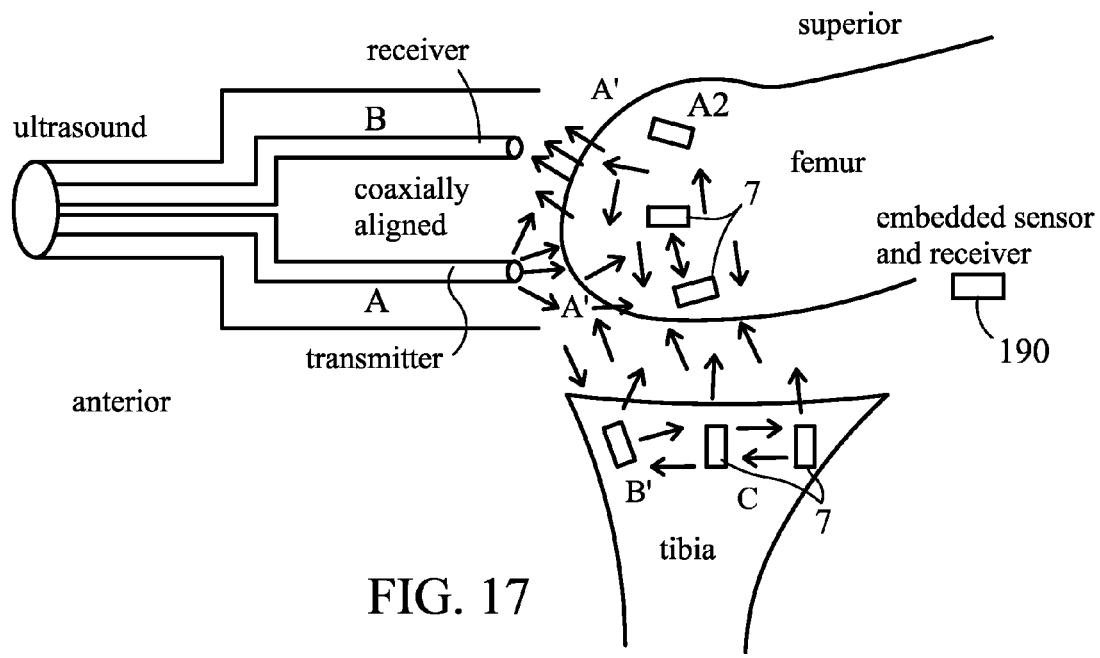
FIG. 17 is a diagrammatic, fragmentary cross-sectional view of a knee joint with ultrasound active sensors according to the invention.
Figure 18:
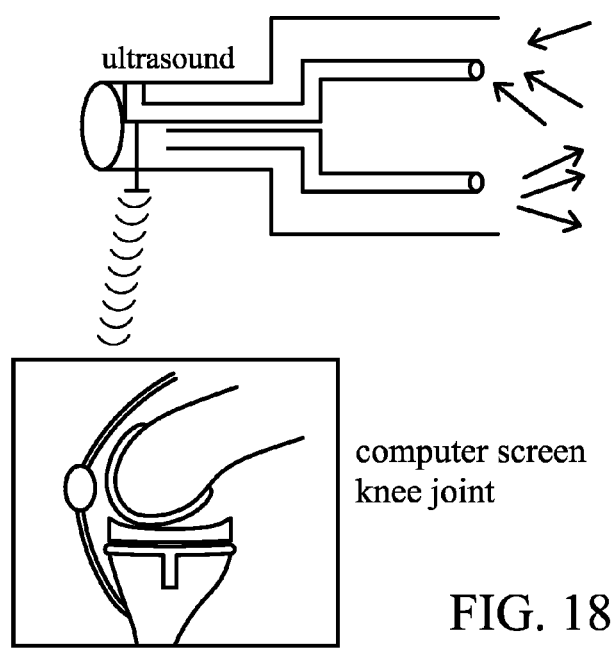
FIG. 18 is a diagrammatic illustration of an ultrasound transmitter and a computer screen showing a knee joint with ultrasound active sensors according to the invention being treated.
Figure 29:
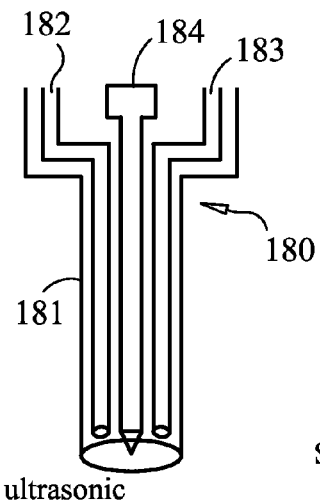
FIG. 29 is a fragmentary, cross-sectional view of a portion of an ultrasonic cannula system according to the invention.

An ultrasonic cannula system 180 allows external non-radiating visualization of the sensor placement as shown in FIG. 29. The cannula 181 houses the transmitter 182 and the receiver 183. The deployment sensor 184 is, then, optimally positioned for insertion. The ultrasonic arm could, then, be used to obtain a rapid topography of the joint surface and depth. The ultrasonic inserter sends energy waves to the multiple embedded sensors 7 that reflect to one another and back to the ultrasonic transducer as shown in FIG. 17. FIG. 17 depicts the ultrasonic sensors 7 using reflection techniques with the sound wave. The sound waves reflect off the end of the bone and the embedded sensor 7 back to the receiver in the ultrasonic inserter. The receiver detects the reflected sound waves and activates the sensor output to a computer screen for visualization as shown in FIG. 18.

The ultrasonic wave also exhibits a thru-beam to the tibia. Here, the transmitter beams the ultrasonic wave to a separate receiver 190. The femur/tibia deflect the beam triggering the receiver output. The added ability of the embedded sensors 7 to continually reflect the ultrasonic beam to the network of sensors 7 allows precise three-dimensional information. The sensor 7 is programmed to compensate for irregular surfaces and variable surface temperature. The measurement of bone is based on the processing of the received ultrasound signals. Speed of the sound and the ultrasound velocity both provide measurements on the basis of how rapidly the ultrasound wave propagates through the bone and the soft tissue. These measures characteristics permit creation of a rapid three-dimensional geometry, which information can be externally sent to the computer system that will allow integration of the prosthesis as shown in FIG. 18.

Figure 30:
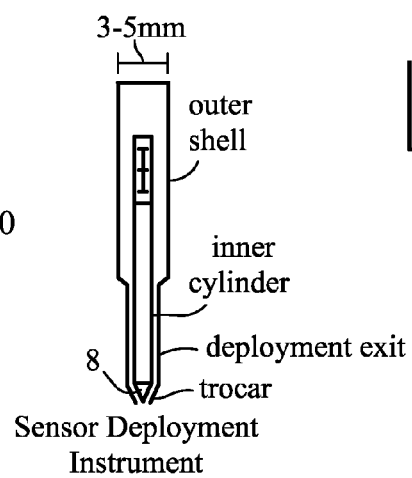
FIG. 30 is a fragmentary, cross-sectional view of a portion of a single sensor cannula deployment device according to the invention.
Figure 31:
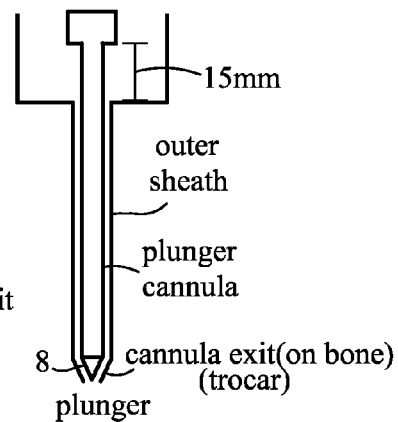
FIG. 31 is a fragmentary, cross-sectional view of a portion of the cannula deployment device of FIG. 31 with multiple sensors.
Figure 32:
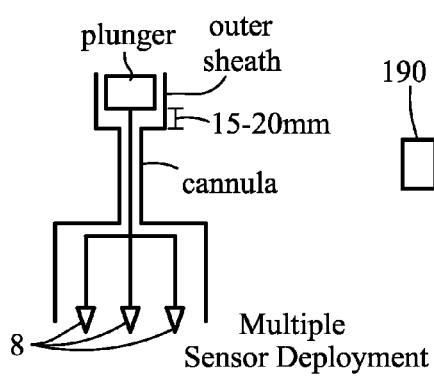
FIG. 32 is a fragmentary, cross-sectional view of a portion of a multi-sensor cannula deployment device according to the invention.
Figure 33:
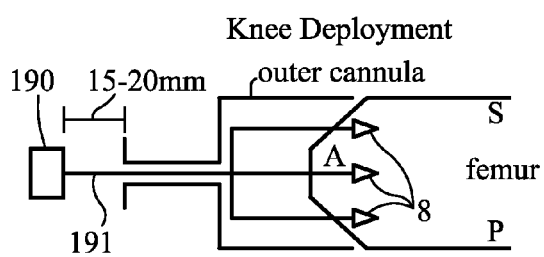
FIG. 33 is a fragmentary side devotional view of an open knee surgery with exclusion of soft tissue and cartilage and bone cuts with sensors according to the invention deployed.
Figure 33:
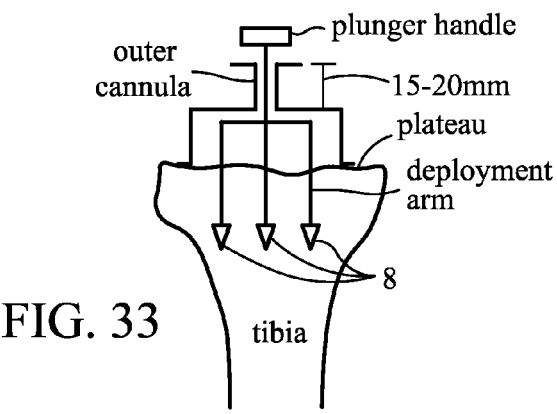

In order for the sensor system to obtain the needed information regarding the spatial three dimensional topography of the joint, a minimum of three sensors are needed to be implanted into each bone that is an integral part of the joint. The deployment of the sensor can be by a single cannula (FIG. 30) with one or several sensors (FIG. 31), or by a multiple sensor deployment cannula (FIG. 32). The sensor would have a calibrated trocar that would penetrate skin, muscle, ligament, tendon, cartilage and bone. FIG. 33 depicts the deployment of the sensors in an open knee surgery where the soft tissue has been excluded and the cartilage and bone cuts have been made. A handle 190 houses a plunger 191 that controls the depth of sensor deployment. See FIGS. 34 to 37. The minimal depth is determined by the amount of cartilage and bone to be cut for the implantation of the prosthesis or implant. For example, in the femur and tibia, a minimum of 10 to 15 millimeters is cut. The sensor is deployed deep with respect to that cut so as not to be dislodged during the procedure and to be able to be used in the post-operative period. The trocar tip would house the elements of the sensor (FIG. 34) and, upon reaching the desired depth of deployment, the sensor 8 is inserted by a release of the locking mechanism (FIG. 19), which can be a screw, or a rotate-to-unlock joint, a break-away, or any other decoupling mechanism.

Figure 12:
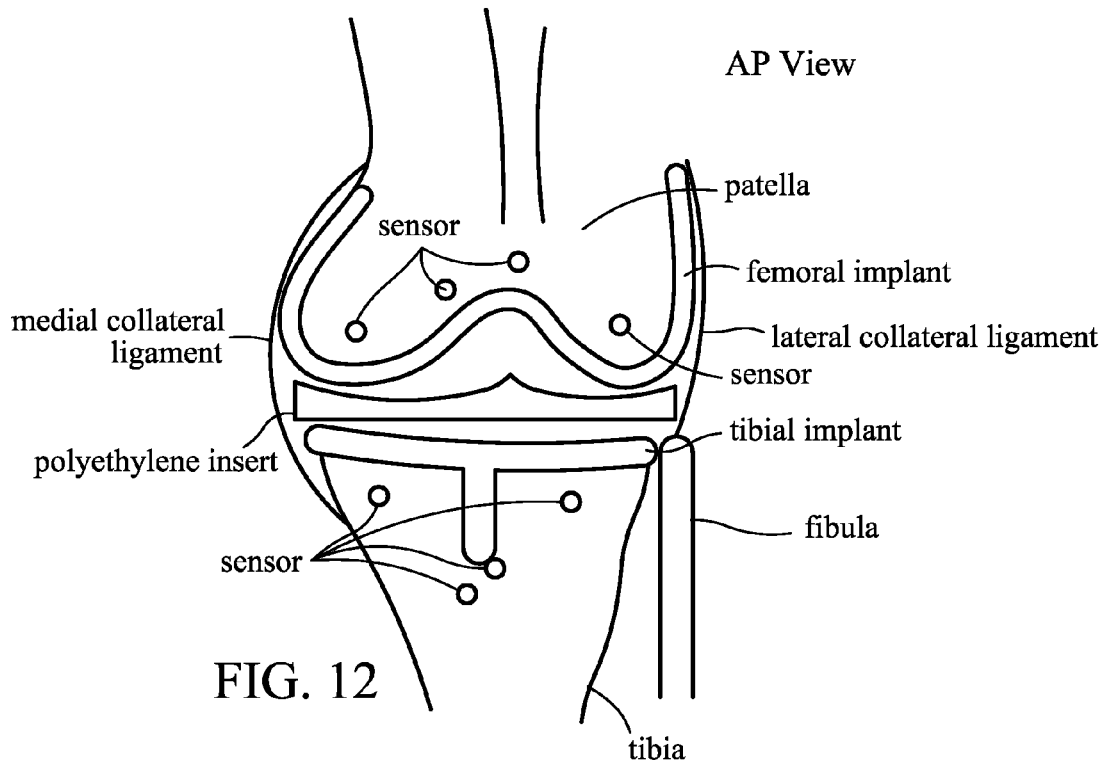
FIG. 12 is a diagrammatic, fragmentary, anterior-posterior, cross-sectional view of a knee joint with sensors according to the invention.
Figure 13:
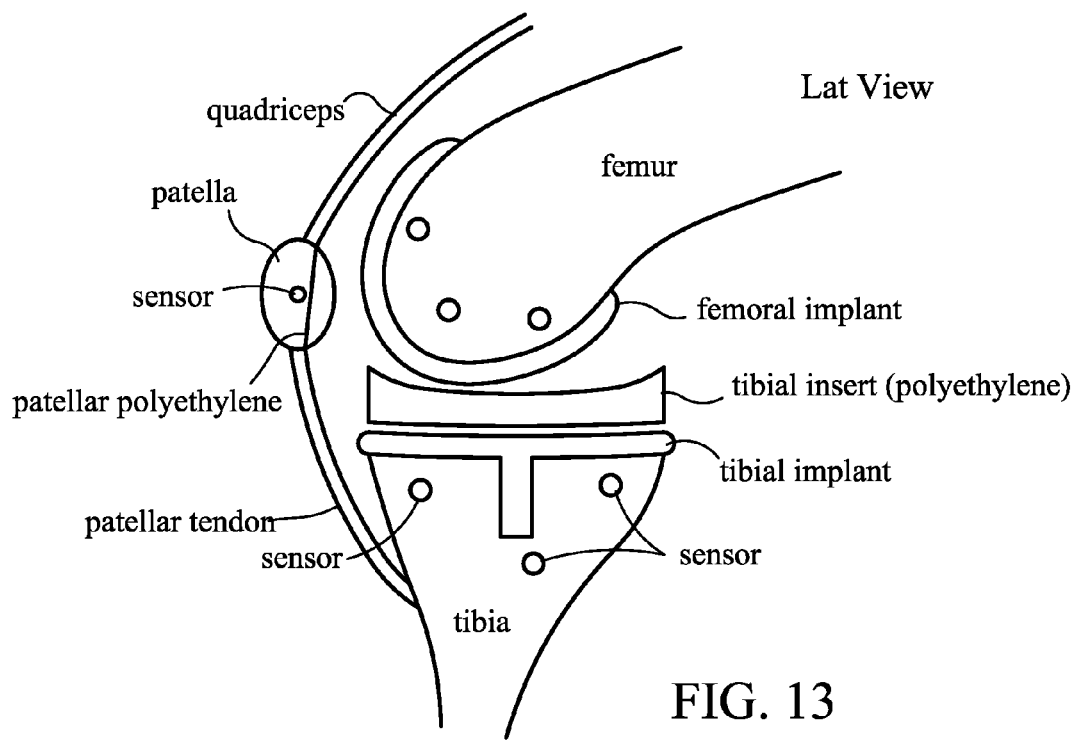
FIG. 13 is a diagrammatic, fragmentary lateral, cross-sectional view of a knee joint with sensors according to the invention.

Once the sensor system has been inserted, the external energy wave that will be used can be ultrasonic, or electromagnetic. The use of the optical array method could, therefore, be avoided. The deflection of the energy through the various mediums (cartilage and bone) and the time element of the energy wave is received by the sensors 8 and/or reflected back to the external receiver. By having the various sensors 8, a three-dimensional model is depicted. This enables the surgeon to embed the sensors (FIG. 33), use them during surgery (FIGS. 18 22) and, then, leave them implanted to be utilized after surgery (FIGS. 12 and 13). Accordingly, the speed of information transmission would be greatly increased and processed.

FIGS. 23 and 24 depict some elements of the knee joint soft tissue. The ACL, the PCL, the medial collateral ligament, and the lateral collateral ligament are important for balancing of a knee joint during surgery. The sensors are embedded into the ligament of a tendon by a clip mechanism (see FIGS. 25 to 28). The information is received and processed by a software system that is integrated into the computer-assisted joint surgery device and presents a visual analogue of an intra-operative joint (FIG. 22). Ligament tension, pressure, shear, etc. is evaluated. A soft-tissue balancing grid aids in the surgeons approach regarding soft tissue releases and component rotation.

FIG. 38 depicts a similar sensor system in the hip. The inserter is similar to a single sensor inserter as shown in FIG. 38, or can be modified as shown in FIG. 38. The inserter is configured to a cannulated acetabular reamer that is used in standard hip surgery. The handle 200 stabilizes the construct and the sensors 8 are deployed by depressing a plunger in the handle 200. FIG. 40 depicts a cup sensor inserter. The cannulated holes allow deployment of the sensor 9. The construct can be modified similar to FIG. 29 to include an ultrasonic component to help visualize the anatomy.

FIGS. 34 to 37 depict the development of "smart" inserters and "smart" instruments. The handle 210 of the inserter/instrument houses an array of sensors 8 to aid in the precise cutting of the bone (FIG. 36) as well as the insertion of the prosthesis and sensors (FIGS. 35 and 37). These sensors 8 are spatially identified by the ultrasonic/electromagnetic transducer and receiver to allow confirmation that the implant/bone interface was prepared appropriately, and that the implant was inserted to the appropriate depth and angle. The stability of a cemented or press fit component could, then, be tested. Sensors implanted onto the prosthesis at the time of surgery or prior to surgery also allow precision insertion and orientation of the prosthesis. Post-operative implant evaluation also is performed.

FIG. 39 depicts the insertion of the sensors 8 into the femur. The sensor 8 can be deployed from the inside-out, from the outside-in, or incorporated into the distal centralizer of the prosthesis and or the canal restrictor.

Figure 41:
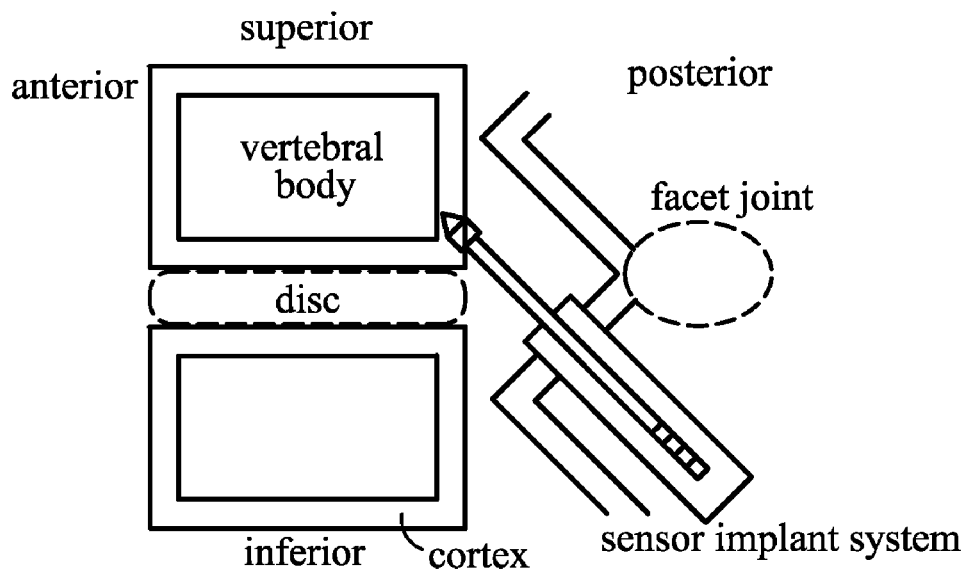
FIG. 41 is a fragmentary, cross-sectional lateral view of two spinal segments with a sensor implantation system according to the invention.
Figure 42:
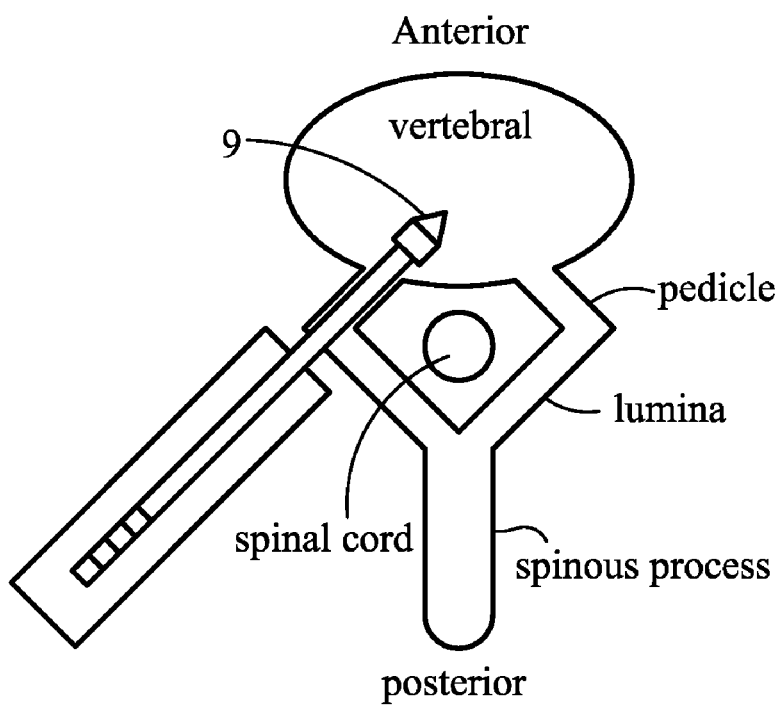
FIG. 42 is a fragmentary, axially cross-sectional view a vertebral level with a sensor implanted through a pedicle.

FIG. 41 depicts the lateral view of two spinal segments. The sensor inserter is shown in a percutaneous manner deploying the sensor into the vertebral body. FIG. 42 depicts an axial view of one vertebral level. The sensor 9 is implanted through the pedicle that has been prepared for instrumentation.

Figure 14:
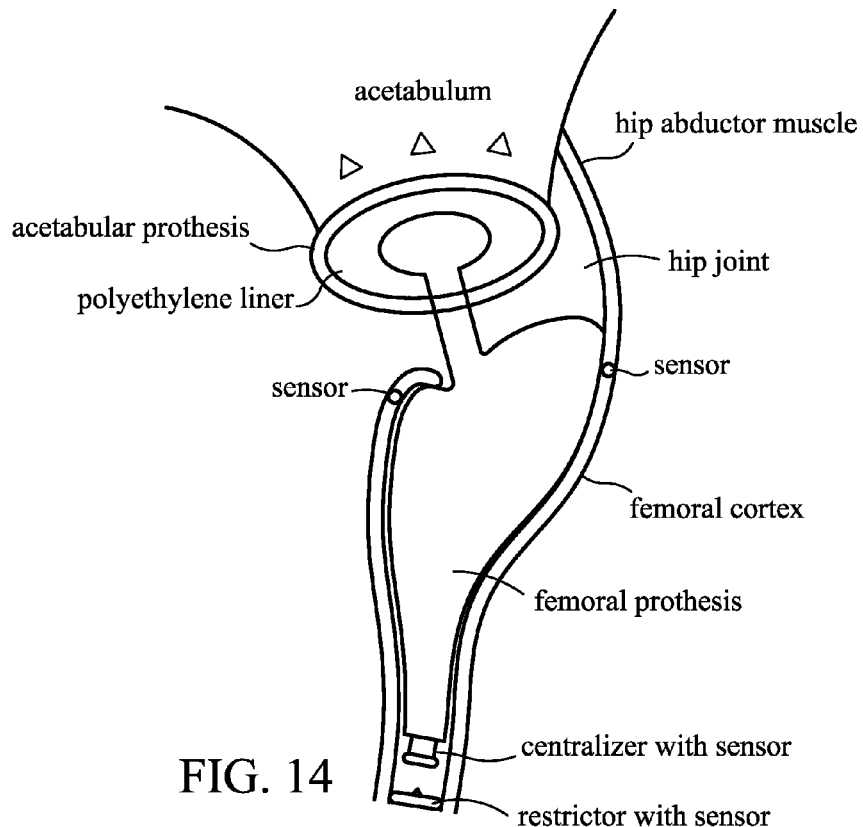
FIG. 14 is a diagrammatic, fragmentary, cross-sectional view of a hip joint with sensors according to the invention.
Figure 15:
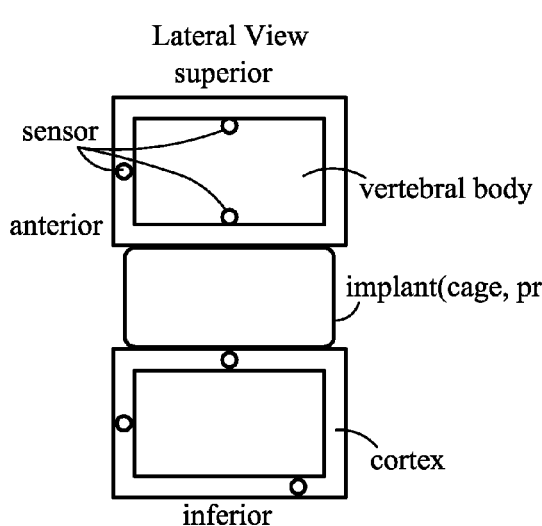
FIG. 15 is a diagrammatic, fragmentary, lateral cross-sectional view of vertebrae with sensors according to the invention.
Figure 16:
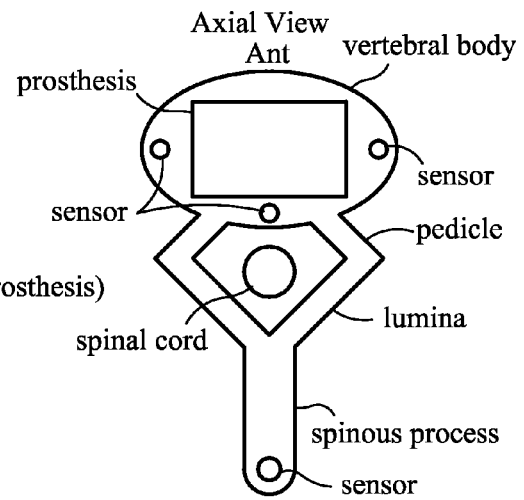
FIG. 16 is a diagrammatic, fragmentary, axial cross-sectional view of a vertebra with sensors according to the invention.

The implanted sensor system following prosthesis insertion is depicted in FIG. 12, an anterior view of the prosthesis, and shows the knee joint, femoral and tibial prostheses, the polyethylene implant, and the embedded sensors. FIG. 13 depicts a lateral view of a knee joint with the prosthesis implanted with sensor system. FIG. 14 depicts a total hip prosthesis with the embedded sensor system. FIG. 15 depicts a lateral view of the embedded sensors within two segments of the vertebrae and an implant. FIG. 16 depicts a sensor system within a vertebral body with a superior (axial) view of a prosthesis/implant.

The sensor system of the present invention can be used pre-operatively to follow the progression of joint pathology and the different treatment interventions. The system can be used intra-operatively to aid in the implantation of the prosthesis/instrumentation/hardware. In the spine, the affects on the neural elements can be evaluated, as well as the vascular changes during surgery, especially corrective surgery. The sensors can, then, be used post-operatively to evaluate changes over time and dynamic changes. The sensor are activated intra-operatively and parameter readings are stored. Immediately post-operatively, the sensor is activated and a baseline is known.

The sensor system allows evaluation of the host bone and tissue regarding, but not limited to bone density, fluid viscosity, temperature, strain, pressure, angular deformity, vibration, vascular/venous/lymphatic flow, load, torque, distance, tilt, shape, elasticity, motion, and others. Because the sensors span a joint space, they can detect changes in the implant function. Examples of implant functions include bearing wear, subsidence, bone integration, normal and abnormal motion, heat, change in viscosity, particulate matter, kinematics, to name a few.

The sensors can be powered by internal batteries or by external measures. A patient could be evaluated in bed at night by a non-contact activation system that can use radio frequency or electromagnetic/ultrasonic energy. The sensor systems' energy signal can penetrate the bed, activate the sensors, and transmit to a receiver that also can be attached to the bed. The sensors can be "upgraded" over time (e.g., with appropriate software enhancements) to evaluate various parameters. The sensors can be modified by an external device, such as a flash drive. For example, a set of embedded sensors can monitor the progression of a spinal fusion that is instrumented. Once a given parameter is confirmed, the same sensors can be re-programmed to monitor the adjacent spinal segments to predict increased stress and, ultimately, subluxation of an adjacent level.

Another feature of the sensor system is that it can rotate through a series of sensor parameters during an evaluation period. An example of such rotation can be evaluation of the bone density as the patient sleeps, and, following this, an evaluation of vascular joint fluid viscosity, and bearing surfaces. Such evaluation can occur on a fixed time sequence on specific intervals or randomly as desired. The information can telemetrically sent to the health care provider by current telephonic devices. Likewise, the patient can be evaluated in the doctor's office with an external sensor activator. The patent could, then, go through a series of motions that allow the physician to evaluate implant function, including such parameters as load, torque, motion, stability, etc.

The software system houses the sensor information in a grid that allows interval comparisons. The physician, then, evaluates the data and functions that fall outside the standard deviations are highlighted, with these parameters being further evaluated.

Even though these sensor systems are discussed herein mainly with respect to the knee, hip, and spine, these systems can be applied to any of the skeletal systems in the body.

Use of the system has been explained in the description of the present invention for a musculoskeletal sensor system. It is to be noted, however, that the present invention is not so limited. The device and method according to the invention can be used with any need.

The foregoing description and accompanying drawings illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

I claim:

1. A method for detecting biometric parameters, which comprises:
    performing a surgical procedure on at least one hip;
    implanting at least one biometric transceiver at the at least one hip;
    transmitting a first energy wave from the transceiver into a procedure area including at least one of the hip and an area adjacent the hip;
    quantitatively assessing the behavior of the energy wave with the transceiver;
    after transmitting the first energy wave:
        transmitting a second energy wave from the transceiver into the procedure area; and
        quantitatively assessing the behavior of the second energy wave;
    wherein at least one of the first and second energy waves are pulsed during transmission in a vibratory manner to stimulate the procedure area in accordance with at least one detected parameter of the procedure area; and
    determining a current status of the at least one parameter of the procedure area selected from the group consisting of pressure, tension, shear, relative position, bone density, fluid viscosity, temperature, strain, angular deformity, vibration, venous flow, lymphatic flow, load, torque, distance, tilt, shape, elasticity, motion, bearing wear, subsidence, bone integration, change in viscosity, particulate matter, kinematics, stability, and vascular flow with the transceiver based upon a comparison between the assessed behavior of the first and second energy waves.

2. The method according to claim 1, which further comprises:
    transmitting data relating to the at least one biometric parameter to an external source; and analyzing the data to evaluate a biometric condition of the at least one hip.

3. The method according to claim 2, which further comprises, based upon the evaluation of the biometric condition of the at least one hip, changing a currently ongoing interoperative procedure at the procedure area.

4. The method according to claim 2, which further comprises, based upon the evaluation of the biometric condition of the at least one hip, chronically monitoring the anatomic condition relating to the procedure area.

5. The method according to claim 1, which further comprises providing a set of the transceivers on the at least one hip.

6. The method according to claim 1, which further comprises providing energy from outside the procedure area to the transceiver to power the transceiver and, thereby, create the energy wave and quantitatively assess the behavior of the energy wave.

7. The method according to claim 6, which further comprises providing the energy through at least one of an electromagnetic couple, a magnetic couple, a capacitive couple, an inductive couple, a sonic couple, an ultrasonic couple, a fiber optic couple, an optical couple, and an infrared couple.

8. The method according to claim 1, which further comprises:
providing a set of the biometric transceivers at the procedure area;
transmitting an energy wave from the transceivers into the procedure area;
quantitatively assessing the behavior of the energy wave with at least one of the transceivers; and
based upon the assessed behavior, determining a current status of the at least one parameter.

9. The method according to claim 1, which further comprises:
providing a set of the biometric transceivers at the procedure area;
transmitting energy waves from the transceivers into the procedure area;
quantitatively assessing the behaviors of the energy waves with the transceivers; and
based upon the assessed behaviors, determining a current status of the at least one parameter.

10. The method according to claim 1, wherein the area adjacent the hip is a second bone different from the hip, and which further comprises transmitting an energy wave from the transceiver, into the second bone, and back to the transceiver.

11. The method according to claim 1, which further comprises carrying out the status determining step by determining a current status of at least two of the group of parameters with the transceiver.

12. The method according to claim 1, which further comprises embedding the at least one biometric transceiver at the at least one hip.

\* \* \* \* \*